United States Patent [19]

Shen

[11] Patent Number: 5,430,193

[45] Date of Patent: Jul. 4, 1995

[54] SYNTHESIS OF 4-HYDROXY-2-ADAMANTANES AND RELATED COMPOUNDS

[75] Inventor: Dong-Ming Shen, Langhorne, Pa.

[73] Assignee: Mobil Oil Corporation, Fairfax, Va.

[21] Appl. No.: 231,092

[22] Filed: Apr. 22, 1994

[51] Int. Cl.[6] .............................................. C07C 45/51
[52] U.S. Cl. ................................... 568/354; 560/256
[58] Field of Search ......................... 560/256; 568/354

[56] References Cited

U.S. PATENT DOCUMENTS

| 4,952,747 | 8/1990 | Alexander et al. | 585/803 |
|---|---|---|---|
| 4,952,748 | 8/1990 | Alexander et al. | 585/803 |
| 4,952,749 | 8/1990 | Alexander et al. | 585/803 |
| 4,982,049 | 1/1991 | Alexander et al. | 585/803 |
| 4,985,403 | 1/1991 | Narula et al. | 560/256 |
| 5,019,660 | 5/1991 | Chapman et al. | 585/22 |
| 5,019,665 | 5/1991 | Partridge et al. | 585/803 |
| 5,021,184 | 6/1991 | Gillaspey et al. | 560/256 |
| 5,053,434 | 10/1991 | Chapman | 521/52 |
| 5,120,899 | 6/1992 | Chen et al. | 585/803 |

OTHER PUBLICATIONS

Yoshida et al, Chem. Abst., vol. 115, #8144p (1991).
Gilbert, E. E., Syn. Commun., 1985, 15(1), 53–6.
Faulkner, D., McKervey, M. A., J. Chem Soc. (C) 1971, 3906–10.
Henkel, J. G.; Spector, J. H., J. Org. Chem. 1983, 48, 3657–61.
Kaufmann, D.; de Meijere, A.; Luk, K.; Overton, K.; Stothers, J., Tetrahedron 1982, 38(7), 977–989.

*Primary Examiner*—James H. Reamer
*Attorney, Agent, or Firm*—Alexander J. McKillop; Dennis P. Santini; Robert B. Furr, Jr.

[57] ABSTRACT

The invention provides a method for converting a lactone of a diamondoid compound to the hydroxyketone of the diamondoid compound wherein the hydroxyl group and the carbonyl group are separated by at least one bridgehead carbon comprising reacting an anhydride containing from about 2 to about 20 carbon atoms with the lactone of the diamondoid compound in the presence of acid.

14 Claims, No Drawings

SYNTHESIS OF 4-HYDROXY-2-ADAMANTANES AND RELATED COMPOUNDS

FIELD OF THE INVENTION

This invention relates to ketone synthesis. More particularly, this invention relates to a method for synthesizing the hydroxyketones and diketones of diamondoid compounds at commercially useful conversion and yield.

BACKGROUND OF THE INVENTION

The hydroxyketones and diketones of diamondoid compounds are useful components in lubricants and traction fluids. Adamantane-2,4-dione, a diketone of the diamondoid compound adamantane, is useful not only as a component in lubricants and traction fluids, but also as an intermediate feedstock for synthesizing complex polymers. More recently, adamantane-2,4-dione has gained importance as a building block for both linear zig-zag polymers and cage structures as taught in U.S. Pat. No. 5,053,434 to Chapman, which is incorporated by reference as if set forth at length herein. The 2,4-dione has, in the past, been relatively difficult to synthesize, and this has made the 2,4-dione both costly and difficult to obtain.

The term "diamondoid compounds" is used herein in its usual sense, to designate a family of polycyclic alkanes including adamantane, diamantane, and triamantane, as well as the higher analogs and their substituted derivatives, examples of which include ethyl- and methyl-substituteddiamondoids. For a survey of the chemistry of diamondoid molecules, see Fort, Raymond C., *Adamantane, The Chemistry of Diamond Molecules* (1976) as well as U.S. Pat. Nos. 5,019,660 to Chapman and Whitehurst and 5,053,434 to Chapman. Diamondoid feedstocks useful in the present invention may be synthesized or may be recovered from natural sources, for example, from certain natural gas deposits.

U.S. Pat. Nos. 4,952,747, 4,952,748, 4,952,749 and 4,982,049 teach methods for recovering diamondoid compounds from a natural gas stream containing the same. U.S. Pat. No. 5,019,665 teaches a method for concentrating diamondoids which are dissolved in a paraffinic solvent. U.S. Pat. No. 5,120,899 teaches a method for recovering diamondoid compounds from a natural gas stream to produce a diamondoid mixture which is substantially free of solvent contamination. The entire text of the patents cited above is incorporated herein by reference for details of diamondoid compound chemistry and production.

Previous methods for synthesizing the hydroxyketones and diketones of the diamondoid compounds (of which adamantane-2,4-dione is one example) required a rigorous intermediate product separation, for example, via column chromatography. See, for example, Gilbert, E. E. Syn. Commun., 1985, 15(1), 53–6, Faulkner, D., McKervey, M. A. J. Chem. Soc. (C) 1971, 3906–10, Henkel, J. G.; Spector, J. H. J. Org. Chem. 1983, 48, 3657–61, and Kaufmann, D.; de Meijere, A.; Luk, K.; Overton, K.; Stothers, J. Tetrahedron, 1982, 38(7), 977–989. While these techniques are effective on a bench scale, it would be desirable to avoid the intermediate product separation in general, and particularly to avoid commercial scale column chromatography. Thus the increasing demand for adamantane-2,4-dione in particular has highlighted the need for a facile, high-yield synthetic route to the diamondoid hydroxyketones and diketones which requires no column chromatography.

SUMMARY OF THE INVENTION

The present invention provides a method for converting a lactone of a diamondoid compound to the hydroxyketone of the diamondoid compound wherein the hydroxyl group and the carbonyl group are separated by at least one bridgehead carbon. The method comprises reacting an anhydride containing from about 2 to about 20 carbon atoms with the lactone of the diamondoid compound in the presence of acid. The anhydride preferably contains from about 4 to about 10 carbon atoms, and more preferably contains about 4 carbon atoms. Examples of useful acid anhydrides include the carboxylic acid anhydrides such as acetic anhydride and trifluoroacetic anhydride, triflic anhydride ($CF_3SO_2)_2O$, and methanesulfonic anhydride ($CH_3SO_2)_2O$. The acid may be any acid which does not inhibit the formation of the hydroxyketone, examples of which include $H_2SO_4$, $H_3PO_4$, $CH_3SO_3H$, $CF_3SO_3H$, $CF_3CO_2H$, and $ArSO_3H$ wherein Ar is a substituted or unsubstituted aryl group.

The present invention further provides a method for converting 4-oxahomoadamantan-5-one to 4-acetoxyadamantanone comprising reaching acetic anhydride with 4-oxahomoadamantan-5-one in the presence of acid at temperature above ambient. The method of the invention may suitably be conducted in a single reaction zone and preferably includes no intermediate separation steps.

In another embodiment, the invention provides a method for converting a lactone of a diamondoid compound to the hydroxyketone of the diamondoid compound wherein the hydroxyl group and the carbonyl group are separated by at least one bridgehead carbon comprising reacting a metal azide such as sodium azide ($NAN_3$) with the lactone of the diamondoid compound in the presence of acid, preferably an alkanesulfonic acid such as methanesulfonic acid.

EXAMPLE 1

Synthesis of 4-Oxahomoadamantan-5-one

Caution: This reaction is quite exothermic. The starting adamantanone should be added in small portions over a period of time. For a detailed description of a method for preparing the Jones reagent, see E. J. Eisenbraun, *Org. Synthesis* Coll. Vol. V, 310, John Wiley and Sons, New York, 1973.

To a 3-L 2-necked round-bottom flask fitted with a reflux condenser and a thermometer were added 1.50 L t-butanol, selenium dioxide (15.53 g. 0.140 mole, MC/B), and 315 mL 30% hydrogen peroxide (104.9 grams, 3.06 mole, Aldrich). The resulting clear solution was heated with a heating mantle to gentle reflux ($\approx 83°$ C.) and stirred magnetically throughout the reaction. Adamantanone (420 grams, 2.80 mole, Aldrich, 99%) was added in small portions from the top of the condenser over a two-hour period with stirring and reflux. An exothermic reaction was observed after each addition. The resulting yellow solution was stirred and refluxed for additional two hours after completing addition. After cooling to room temperature, the reaction mixture was transferred into a separatory funnel containing 1.5 L saturated brine and 500 mL de-ionized water. About 1 L of chloroform was added and the mixture was shaken. The aqueous (bottom) layer was separated and extracted with 2×100 mL chloroform. The combined organic layers were washed with 1 L each of water and saturated brine. The solvents were removed on a rotary evaporator after drying over anhydrous sodium sulfate, giving 485.45 grams of white solid. GC analysis of this crude product showed one peak accounting for 98.8% of the integrated area. Carbon-13 NMR showed it to be pure 4-Oxahomoadamantan-5-one: 180.6, 73.9, 41.6, 36.1, 34.1, 31.2, 26.1 ppm. The yield of this step is assumed to be 99% based on GC. The crude product was used in the following Examples without further purification.

EXAMPLE 2

Conversion of 4-Oxahomoadamantan-5-one to 4-Acetoxyadamantanones

A mixture containing 4-Oxahomoadamantane-5-one (12.5 grams, 75.3 mmol), 40 mL acetic anhydride, and 100 mL cyclohexane was charged to a 250-mL round-bottom flask and heated to reflux with a heating mantle. Concentrated sulfuric acid (0.52 grams, 5.4 mmol) was added dropwise from the top of the condenser with magnetic stirring. After 40 hours of reflux, about 5% of the 4-Oxahomoadamantan-5-one was converted to the products. More concentrated $H_2SO_4$ was added (15.8 grams, 158 mmol) in the same fashion. This separated the reaction mixture into a top grayish layer of mostly cyclohexane and a black bottom layer. Refluxing was continued for additional 6 hrs, when GC analysis of the top layer showed that the reaction was complete. After cooling, the reaction mixture was transferred into a separatory funnel and the layers were separated. The dark bottom layer was extracted with 3×50 mL cyclohexane. The combined cyclohexane solutions was washed with 100 mL each of 1N NaOH and saturated brine. GC analysis of the solution showed >99% pure two isomers of 4-Acetoxyadamantanones. After drying over anhydrous $Na_2SO_4$, removal of solvent gave 4.03 gram of 4-Acetoxyadamantanone as a yellowish oil. Crushed ice was added to the conc. $H_2SO_4$ layer separated from the reaction mixture. The resulting solution was diluted with water to $\approx 500$ mL and extracted with 4×100 mL $CH_2Cl_2$. The combined yellow $CH_2Cl_2$ solutions was washed with 1N NaOH (2 ×200 mL), water (100 mL), and saturated brine (100 mL). GC analysis of the solution showed that it was predominantly 4-Acetoxyadamantanone with small amounts of 4-Hydroxyadamantanones. Removal of solvent by rotary evaporation gave 7.24 grams of a red oil.

EXAMPLE 3

Conversion of 4-Oxahomoadamantan-5-one to 4-Hydroxyadamantanone

A solution of lactone 4-Oxahomoadamantan-5-one (445.8 grams, 2.52 mole, 94%) in 1.52 L acetic anhydride (1643 g. 16.1 mole) was prepared in a 3-L 2-neck round bottom flask fitted with a thermometer and a reflux condenser having a $N_2$ bubbler. The flask was heated with a heating mantle to 50° C. Concentrated $H_2SO_4$ (52.8 grams, 20.2 mL, 0.528 mole) was added drop-wise from the top of the condenser with magnetic stirring over 15 min. This raised the temperature to 75° C. and turned the mixture opaque. The reaction mixture was occasionally sampled for GC analyses. After 42 hrs of heating at 110°$\approx$125° C., the reaction was complete based on a GC analysis. Over the next 45 min., NaOAc.3$H_2O$ crystals (180 grams, 1.32 mole) was added in small portions from the top of the condenser with stir and reflux to remove $H_2SO_4$ from the reaction mixture. The reaction mixture was distilled under partial vacuum ($\approx 10$ in. Hg) to remove about 1300 gram distillate with b.p. of 80°$\approx$90° C. at pot temperatures of 100°$\approx$140° C. Water (100 mL) was added very slowly from the top of the condenser to the residue in the flask with reflux over 45 min. to hydrolyze the remaining acetic anhydride. This dark reaction mixture was transferred into a 5-L 4-necked round-bottom flask using $\approx 1.5$ L of water. The flask was fitted with a mechanical stirrer and a reflux condenser. A total of 300 gram NaOH pellets were added drop-wise in the form of 25% aqueous solution to the flask from a pressure-equalized addition funnel to the flask with stir and reflux in 6 portions over a period of about 12 hours. The pH of the reaction mixture was monitored to maintain basicity. Reflux was continued for an additional 16 hours after the last portions of NaOH was added. A large tar-ball was formed during the reaction; it dissolved at the end of the hydrolysis. The progress of the hydrolysis was monitored by GC analyses of aliquots taken periodically from the reaction mixture.. At the end of the reaction, the mixture was cooled to room temperature and filtered through an 1" pad of Celite to remove some black gum. The filtered gum was repeatedly washed with $CH_2Cl_2$ (a total of $\approx 10$ L). The filtrate was transferred into a separatory funnel and extracted with $CH_2Cl_2$ (20×1 L). The $CH_2Cl_2$ extract was washed with water and saturated brine, dried over anhydrous $Na_2SO_4$, and rotary-evaporated to give $\approx 350$ gram black solid as crude 4-Hydroxyadamantanones. This crude product was filtered through $\approx 650$ gram silica gel with 6 L acetone to give 340.82 gram dark brown solid. GC analysis of this showed that the solid was 98% pure 4-hydroxy-2-adamantanones (77% yield).

EXAMPLE 4

Preparation and Purification of Crude Adamantane-2,4-dione

The sample of crude 4-hydroxy-2-adamantanones prepared above (340.82 g) was dissolved in 3 L of acetone in a 5-L 4-necked round-bottom flask fitted with a mechanical stirrer, a pressure-equalized addition funnel, a thermometer immersed in the reaction mixture, and a stopper. About 570 mL Jones reagent was prepared from 150 gram $CrO_3$, 245 gram conc. $H_2SO_4$, and water using a standard procedure and transferred into the funnel. The temperature of the mixture was maintained at 8°$\approx$11° C. by an water bath at about 4° C. About 500 mL of the Jones reagent was added drop-wise with stir over a three-hour period with stir and cooling. The initial dark brown solution turned to greenish brown soon after addition had began. Near the end of the addition, the mixture acquired an orange tint. One hour after the start of the addition, 100 mL water was added to the reaction mixture to dissolve a solid mass formed at the bottom of the flask. GC analysis of the reaction mixture showed about 1.3% 4-hydroxyadamantanones remaining. After stirring overnight, the amount of 4-hydroxyadamantanones in the solution increased to 2.3% based on GC analysis. The mixture was cooled to 14°$\approx$17° C. and the remaining Jones reagent ($\approx 70$ mL) was added drop-wise with stir over a three-hour period. The resulting mixture was stirred for additional 40 hours during which it warmed up to room temperature. GC analysis of an aliquot showed a product/starting material ratio of ≈300. The top acetone solution was decanted from the bottom green gum. The gum was washed with acetone several times. The acetone was removed with rotary evaporation and partition the resulting residue between water and $CH_2Cl_2$ (2 L). The methylene chloride solution was washed with 5% $NaHCO_3$, EDTA solution, water, and saturated brine, and was then dried over anhydrous $Na_2SO_4$. GC analysis of this solution (A) showed 98% adamantane-2,4-dione and 0.6% 4-hydroxyadamantanones. The green gum from the reaction flask was dissolved in 1.5 L of water and extracted with $CH_2Cl_2$ (3×150 mL). The combined extract was washed with EDTA solution and saturated brine, and was then dried over anhydrous $Na_2SO_4$. GC analysis of this solution showed that it contained 93% and 7% of adamantane-2,4-dione and 4-hydroxy-2-adamantanones, respectively. Removal of solvent gave about 2.1 gram solid. This product was combined with solution A above to give about 329 gram brown solid as crude product after removal of solvent. This was sublimed using an Aldrich Kügelrohr with two traps cooled with ice-water and dry-ice/isopropanol at 0.1 mm-Hg and a pot temperature of 90°-100° C. A total of 275.6 grams of a white solid was obtained from the two traps. GC analysis of a solution of this product showed that it contained 96.5% adamantane-2,4-dione and 1.1% 4-hydroxyadamantanones. The dark residue in the original flask was filtered through about 400 gram silica gel with 3 L of 1:1 acetone/hexanes to give 20.6 gram oily solid, which on Kügelrohr sublimation gave another 7.5 gram product containing 92.3% adamantane-2,4-dione and 2.5% 4-hydroxy-2-adamantanones based on GC analysis.

Attempts to recrystallize the products in EtOAc, EtOH, and MeOH failed to remove the alcohols. The above dione fractions were then combined with 16.04 gram of 98.0% pure adamantane-2,4-dione containing 1.2% 4-hydroxyadamantanones obtained in a smaller scale run and dissolved in 2.0 L acetone. A GC analysis of this solution showed that it contained 97.5% adamantane-2,4-dione and 1.1% 4-hydroxyadamantanones.

A total of 55 mL of Jones reagent was prepared from 15.0 gram $CrO_3$ using the standard method. This was added drop-wise intermittently to the acetone solution kept at about 15° C. with magnetic stir until the orange color persisted. GC assay of the reaction mixture showed no 4-hydroxy-2-adamantanones in the mixture. A total of 20 mL of Jones reagent was added. After stirring for an additional half hour, 5 mL of isopropanol was added to the flask to decompose excess Jones reagent. Add 15 gram $NaHCO_3$ to the flask with stir. The reaction mixture was concentrated on a rotary evaporator to remove about half of the acetone, mixed with approximately equal volume of hexanes, dried over anhydrous $Na_2SO_4$, and filtered through about 500 gram silica gel with 1:1 acetone/hexanes to remove chromium residue. Removal of solvents from the filtrate gave 297.95 gram slightly yellowish solid, which is >99% pure adamantane-2,4-dione based on GC analysis. Recrystallization of the crude product in 550 mL of EtOAc gave 99.65 gram colorless crystalline solid product, which was shown to be >99.7% pure adamantane-2,4-dione by GC analysis. A second crop from 350 mL EtOAc gave 74.43 gram adamantane-2,4-dione with >99.8% purity based on GC. The mother liquor from the second recrystallization contained 121.08 grams of a yellowish product containing >97.6% adamantane-2,4-dione with small amounts of hydroxyadamantane-2,4-dione and 4-oxahomoadamantane as the main impurities.

Changes and modifications in the specifically described embodiments can be carried out without departing from the scope of the invention which is intended to be limited only by the scope of the appended claims.

What is claimed is:

1. A method for converting a lactone of a diamondoid compound to the hydroxyketone of the diamondoid compound wherein the hydroxyl group and the carbonyl group are separated by at least one bridgehead carbon comprising reacting an anhydride containing from about 2 to about 20 carbon atoms with the lactone of the diamondoid compound in the presence of acid and then hydrolyzing the intermediate keto-esters.

2. The method of claim 1 wherein said reaction is carried out in a nonpolar solvent at reflux temperature.

3. The method of claim 2 wherein said nonpolar solvent comprises a cycloalkane.

4. The method of claim 3 wherein said cycloalkane comprises cyclohexane.

5. The method of claim 1 wherein said anhydride contains from about 4 to about 10 carbon atoms.

6. The method of claim 5 wherein said anhydride comprises acetic anhydride.

7. The method of claim 1 wherein said diamondoid compound is selected from the group consisting of adamantane, diamantane, and triamantane.

8. The method of claim 7 wherein said diamondoid compound comprises adamantane.

9. A method for converting 4-oxahomoadamantan-5-one to 4-acetoxyadamantanone comprising reaching acetic anhydride with 4-oxahomoadamantan-5-one in the presence of acid at temperature above ambient.

10. The method of claim 9 wherein said reaction is carried in nonpolar solvent at reflux temperature.

11. The method of claim 10 wherein said acid is a Bronsted acid selected from the group consisting of $H_2SO_4$, $H_3PO_4$, $CH_3SO_3H$, $CF_3SO_3H$, $CF_3CO_2H$, and $ArSO_3H$ wherein Ar is a substituted or unsubstituted aryl group.

12. A method for converting a lactone of a diamondoid compound to the hydroxyketone of the diamondoid compound wherein the hydroxyl group and the carbonyl group are separated by at least one bridgehead carbon comprising reacting a metal azide with the lactone of the diamondoid compound in the presence of acid.

13. The method of claim 12 wherein said acid comprises an alkanesulfonic acid.

14. The method of claim 12 wherein said acid comprises methanesulfonic acid.

* * * * *